(12) United States Patent
Schoenberg

(10) Patent No.: US 9,678,636 B2
(45) Date of Patent: Jun. 13, 2017

(54) MODALITIES FOR BROKERED ENGAGEMENTS

(71) Applicant: American Well Corporation, Boston, MA (US)

(72) Inventor: Roy Schoenberg, Boston, MA (US)

(73) Assignee: American Well Corporation, Boston, MA (US)

( * ) Notice: Subject to any disclaimer, the term of this patent is extended or adjusted under 35 U.S.C. 154(b) by 0 days.

(21) Appl. No.: 13/792,459

(22) Filed: Mar. 11, 2013

(65) Prior Publication Data

US 2014/0200910 A1 Jul. 17, 2014

Related U.S. Application Data

(60) Provisional application No. 61/753,528, filed on Jan. 17, 2013.

(51) Int. Cl.
| | |
|---|---|
| *G06F 19/00* | (2011.01) |
| *G06Q 50/22* | (2012.01) |
| *G06F 3/0484* | (2013.01) |
| *H04L 29/06* | (2006.01) |
| *G06Q 10/10* | (2012.01) |

(52) U.S. Cl.
CPC .......... *G06F 3/0484* (2013.01); *G06F 19/327* (2013.01); *G06F 19/3418* (2013.01); *G06Q 10/10* (2013.01); *G06Q 50/22* (2013.01); *H04L 65/403* (2013.01)

(58) Field of Classification Search
CPC ..... G06Q 50/22–50/24; G06F 19/3418; G06F 19/327
See application file for complete search history.

(56) References Cited

U.S. PATENT DOCUMENTS

| | | | |
|---|---|---|---|
| 5,801,755 | A | 9/1998 | Echerer |
| 5,911,687 | A | 6/1999 | Sato et al. |
| 5,995,939 | A | 11/1999 | Berman et al. |
| 6,151,581 | A | 11/2000 | Kraftson et al. |
| 6,223,165 | B1 | 4/2001 | Lauffer |
| 6,322,502 | B1 | 11/2001 | Schoenberg et al. |
| 6,381,576 | B1 | 4/2002 | Gilbert |
| 6,463,417 | B1 | 10/2002 | Schoenberg |
| 6,519,570 | B1 | 2/2003 | Faber et al. |
| 6,523,010 | B2 | 2/2003 | Lauffer |
| 6,546,372 | B2 | 4/2003 | Lauffer |
| 6,549,889 | B2 | 4/2003 | Lauffer |
| 6,735,569 | B1 | 5/2004 | Wizig |

(Continued)

FOREIGN PATENT DOCUMENTS

| | | |
|---|---|---|
| EP | 1549025 | 6/2005 |
| JP | 2001-306695 | 11/2001 |

(Continued)

OTHER PUBLICATIONS

IBM, "Method to support 'on demand' selection of service provider." May 8, 2007. IP.com No. IPCOM000152643D.*

(Continued)

*Primary Examiner* — Sheetal R Paulson
(74) *Attorney, Agent, or Firm* — Fish & Richardson P.C.

(57) ABSTRACT

Described are techniques for providing broker services to consumers with service providers according to a user selected modality type including an anonymous user modality type.

19 Claims, 13 Drawing Sheets

(56) References Cited

U.S. PATENT DOCUMENTS

| | | |
|---|---|---|
| 6,801,899 B2 | 10/2004 | Lauffer |
| 7,069,028 B2 | 6/2006 | Natsuno |
| 7,172,120 B2 | 2/2007 | Schoenberg |
| 7,249,045 B2 | 7/2007 | Lauffer |
| 7,308,422 B1 | 12/2007 | Faber et al. |
| 7,373,159 B2 | 5/2008 | Natsuno |
| 7,412,396 B1 | 8/2008 | Haq |
| 7,478,049 B2 | 1/2009 | Schoenberg |
| 7,590,550 B2 | 9/2009 | Schoenberg |
| 7,653,558 B2 | 1/2010 | Schoenberg |
| 7,729,938 B2 | 6/2010 | Lauffer |
| 7,774,377 B2 | 8/2010 | Schoenberg |
| 7,840,418 B2 | 11/2010 | Schoenberg |
| 7,865,377 B2 | 1/2011 | Schoenberg |
| 7,895,061 B2 | 2/2011 | Schoenberg |
| 7,933,783 B2 | 4/2011 | Schoenberg |
| 7,937,275 B2 | 5/2011 | Schoenberg |
| 7,945,456 B2 | 5/2011 | Schoenberg |
| 8,155,977 B2 | 4/2012 | Schoenberg |
| 8,396,735 B2 | 3/2013 | Lauffer |
| 2001/0051765 A1 | 12/2001 | Walker et al. |
| 2002/0010608 A1 | 1/2002 | Faber et al. |
| 2002/0165732 A1 | 11/2002 | Ezzeddine et al. |
| 2003/0004756 A1 | 1/2003 | Okamoto et al. |
| 2003/0023508 A1 | 1/2003 | Deep |
| 2003/0093294 A1 | 5/2003 | Passantino |
| 2003/0126205 A1 | 7/2003 | Lurie |
| 2003/0144580 A1 | 7/2003 | Iliff |
| 2003/0195838 A1 | 10/2003 | Henley |
| 2004/0019579 A1 | 1/2004 | Herz et al. |
| 2004/0111298 A1 | 6/2004 | Schoenberg |
| 2004/0111622 A1 | 6/2004 | Schoenberg |
| 2004/0152952 A1 | 8/2004 | Gotlib et al. |
| 2004/0153343 A1 | 8/2004 | Gotlib et al. |
| 2004/0181430 A1 | 9/2004 | Fotsch et al. |
| 2005/0021519 A1* | 1/2005 | Ghouri ................. G06F 19/326 |
| 2005/0065813 A1 | 3/2005 | Mishelevich et al. |
| 2005/0108052 A1 | 5/2005 | Omaboe |
| 2005/0125252 A1 | 6/2005 | Schoenberg |
| 2005/0125254 A1 | 6/2005 | Schoenberg |
| 2005/0125487 A1 | 6/2005 | O'Connor et al. |
| 2005/0182743 A1 | 8/2005 | Koenig |
| 2005/0234745 A1 | 10/2005 | Schoenberg |
| 2005/0288965 A1 | 12/2005 | Van Eaton et al. |
| 2006/0106644 A1 | 5/2006 | Koo et al. |
| 2006/0116900 A1 | 6/2006 | Jensen |
| 2006/0122850 A1 | 6/2006 | Ward et al. |
| 2006/0136264 A1 | 6/2006 | Easton et al. |
| 2006/0161457 A1 | 7/2006 | Rapaport et al. |
| 2006/0200356 A1 | 9/2006 | Wan |
| 2007/0088580 A1 | 4/2007 | Richards, Jr. |
| 2007/0136095 A1 | 6/2007 | Weinstein |
| 2007/0150372 A1 | 6/2007 | Schoenberg |
| 2008/0065414 A1 | 3/2008 | Schoenberg |
| 2008/0275311 A1* | 11/2008 | Haq ....................... G06Q 10/10 600/300 |
| 2009/0063188 A1 | 3/2009 | Schoenberg |
| 2009/0089074 A1 | 4/2009 | Schoenberg |
| 2009/0089085 A1 | 4/2009 | Schoenberg |
| 2009/0089097 A1 | 4/2009 | Schoenberg |
| 2009/0089147 A1 | 4/2009 | Schoenberg |
| 2009/0313044 A1 | 12/2009 | Haque et al. |
| 2010/0279718 A1* | 11/2010 | Borve ........................... 455/466 |
| 2011/0288884 A1* | 11/2011 | Algoo et al. ..................... 705/3 |
| 2012/0130742 A1* | 5/2012 | Church ................ G06Q 50/24 705/3 |
| 2013/0060576 A1* | 3/2013 | Hamm ................ G06F 19/3418 705/2 |
| 2013/0182834 A1 | 7/2013 | Lauffer |

FOREIGN PATENT DOCUMENTS

| | | |
|---|---|---|
| JP | 2002-032602 | 1/2002 |
| JP | 2002-092173 | 3/2002 |
| JP | 2002-230341 | 8/2002 |
| JP | 2005-353088 | 12/2005 |
| JP | 2006-79195 | 3/2006 |
| WO | WO 00/57326 | 9/2000 |
| WO | WO 01/22718 | 3/2001 |

OTHER PUBLICATIONS

U.S. Appl. No. 12/031,018, filed Feb. 14, 2008, Schoenberg.
U.S. Appl. No. 12/038,110, filed Feb. 27, 2008, Schoenberg.
U.S. Appl. No. 12/059,165, filed Mar. 31, 2008, Schoenberg.
U.S. Appl. No. 12/061,338, filed Apr. 2, 2008, Schoenberg.
U.S. Appl. No. 12/098,669, filed Apr. 7, 2008, Schoenberg.
U.S. Appl. No. 12/098,732, filed Apr. 7, 2008, Schoenberg.
U.S. Appl. No. 12/098,758, filed Apr. 7, 2008, Schoenberg.
U.S. Appl. No. 12/105,784, filed Apr. 18, 2008, Schoenberg.
U.S. Appl. No. 12/117,324, filed May 8, 2008, Schoenberg.
U.S. Appl. No. 12/129,172, filed May 29, 2008, Schoenberg.
U.S. Appl. No. 12/140,760, filed Jun. 17, 2008, Schoenberg.
U.S. Appl. No. 12/256,216, filed Oct. 22, 2008, Schoenberg.
U.S. Appl. No. 60/748,966, filed Dec. 9, 2005, Ronald S. Weinstein.
Decision in Application No. IPR2015-00924, dated Sep. 14, 2015, pp. 1-13.
Scheduling Order in Application No. IPR2015-00924, dated Sep. 14, 2015, pp. 1-7.
Application in corresponding U.S. Appl. No. 11/763,680 dated Jun. 15, 2007, pp. 1-576.
Notice of Filing Date Accorded to Petition and Time for Filing Patent Owner Preliminary Response in Application No. IPR2015-00924, dated Apr. 1, 2015, pp. 1-3.
Petition for Inter Partes Review of Claims 10-11, 23, and 30 of U.S. Patent No. 7,590,550 in Application No. IPR2015-00924, dated Mar. 24, 2015, pp. 1-53.
Patent Owner American Well Corporation's Mandatory Notices in Application No. IPR2015-00924, dated Apr. 17, 2015, pp. 1-4.
Petitioner's Revised Mandatory Notice regarding Related Matters, in Application No. IPR2015-00924, dated Jul. 7, 2015 pp. 1-4.
Teladoc, Exhibit 1004, in Application No. IPR2016-00101, downloaded on Oct. 26, 2015, pp. 1-5.
Murphy and Bird, "Telediagnosis: A New Community Health Resource, Observations on the Feasibility of Telediagnosis Based on 1000 Patient Transactions," 64(2):113-119 (1974).
Declaration of Scott Silverman in Support of Petition for Inter Partes Review of Claims 1-42 of U.S. Patent No. 7,835,928, in Application No. IPR2016-00101, dated Oct. 28, 2015, pp. 1-52.
Petition for Inter Partes Review of Claims 1-42 of U.S. Pat. No. 7,835,928 in Application No. IPR2016-00101, dated Oct. 28, 2015, pp. 1-63.
Declaration of Christopher R. Dillon in Support of Patent Owner's Motion for Pro Hac Vice Admission, in Application No. IRP2016-00101, dated Jan. 5, 2016, pp. 1-8.
Patent Owner American Well Corp.'s Motion for Pro Hac Vice Admission, in Application No. IRP2016-00101, dated Jan. 5, 2016, pp. 1-5.
Patent Owner American Well Corporation's Mandatory Notices, in Application No. IRP2016-00101, dated Nov. 18, 2015, pp. 1-4.
Patent Owner American Well Corp.'s Motion for Pro Hac Vice Admission, in Application No. IPR2015-00924, dated Jan. 5, 2016, pp. 1-5.
Declaration of Christopher R. Dillon in Support of Patent Owner's Motion for Pro Hac Vice Admission, in Application No. IRP2015-00924, dated Jan. 5, 2016, pp. 1-8.
Patent Owner American Well Corporation's Updated Mandatory Notices in Application No. IPR2015-00924, dated Nov. 18, 2015, pp. 1-3.
Declaration of Dr. Ronald S. Weinstein, M.D., in Application No. IRP2015-00924, dated Nov. 23, 2015, pp. 1-74.
Declaration of Scott Silverman in Support of Petition for Inter Partes Review of Claims 1-9, 12-22, and 24-29 of U.S. Patent No. 7,590,550, in Application No. IPR2016-00100, pp. 1-3.
Texas Medical Board in Application No. IPR2015-00924, dated Nov. 21, 2015, pp. 1-6.

(56) References Cited

OTHER PUBLICATIONS

The American Heritage Dictionary in Application No. IPR2015-00924, pp. 1-3.
Merriam-Webster's Collegiate Dictionary in Application No. IPR2015-00924, pp. 1-3.
Shorter Oxford English Dictionary in Application No. IPR2015-00924, pp. 1-4.
U.S. Appl. No. 09/918,413 dated Jul. 30, 2001 in Application No. IPR2015-00924, pp. 1-544.
1395dd Examination and treatment for emergency medical conditions and women in labor, dated Oct. 21, 2011, pp. 1-7 in Application No. IPR2015-00924.
Medicare Program Clarifying Policies Related to the Responsibilities of Medicar dated Sep. 9, 2003, pp. 1-74 in Application No. IPR2015-00924.
843G288 Diagnostic services staff time and availability, p. 1 in Application No. IPR2015-00924.
19 CSR 30-20.092 Emergency Services in Hospitals, pp. 1-4 in Application No. IPR2015-00924.
Patent Owner American Well Corp. Response in Application No. IPR2015-00924, pp. 1-56, dated Nov. 23, 2015.
Patent Owner American Well Corp.'s Motion for Pro Hac Vice Admission in Application No. IPR2016-00100, dated Jan. 5, 2016, pp. 1-5.
Declaration of Christopher R. Dillon in Support of Patent Owner's Motion for Pro Hac Vice Admission, in Application No. IRP2016-00100, dated Jan. 5, 2016, pp. 1-8.
Patent Owner American Well Corporation's Mandatory Notices in Application No. IRP2016-00100, dated Nov. 18, 2015, pp. 1-4.
Declaration of Scott Silverman in Support of Petition for Inter Partes Review of Claims 1-9, 12-22, and 24-29 of U.S. Patent No. 7,590,550, in Application No. IPR2016-00100, pp. 1-57.
Petition for Inter Partes Review of Claims 1-9, 12-22, and 24-29 of U.S. Patent No. 7,590,550 in Application No. IPR2016-00100, dated Oct. 28, 2015, pp. 1-59.

\* cited by examiner

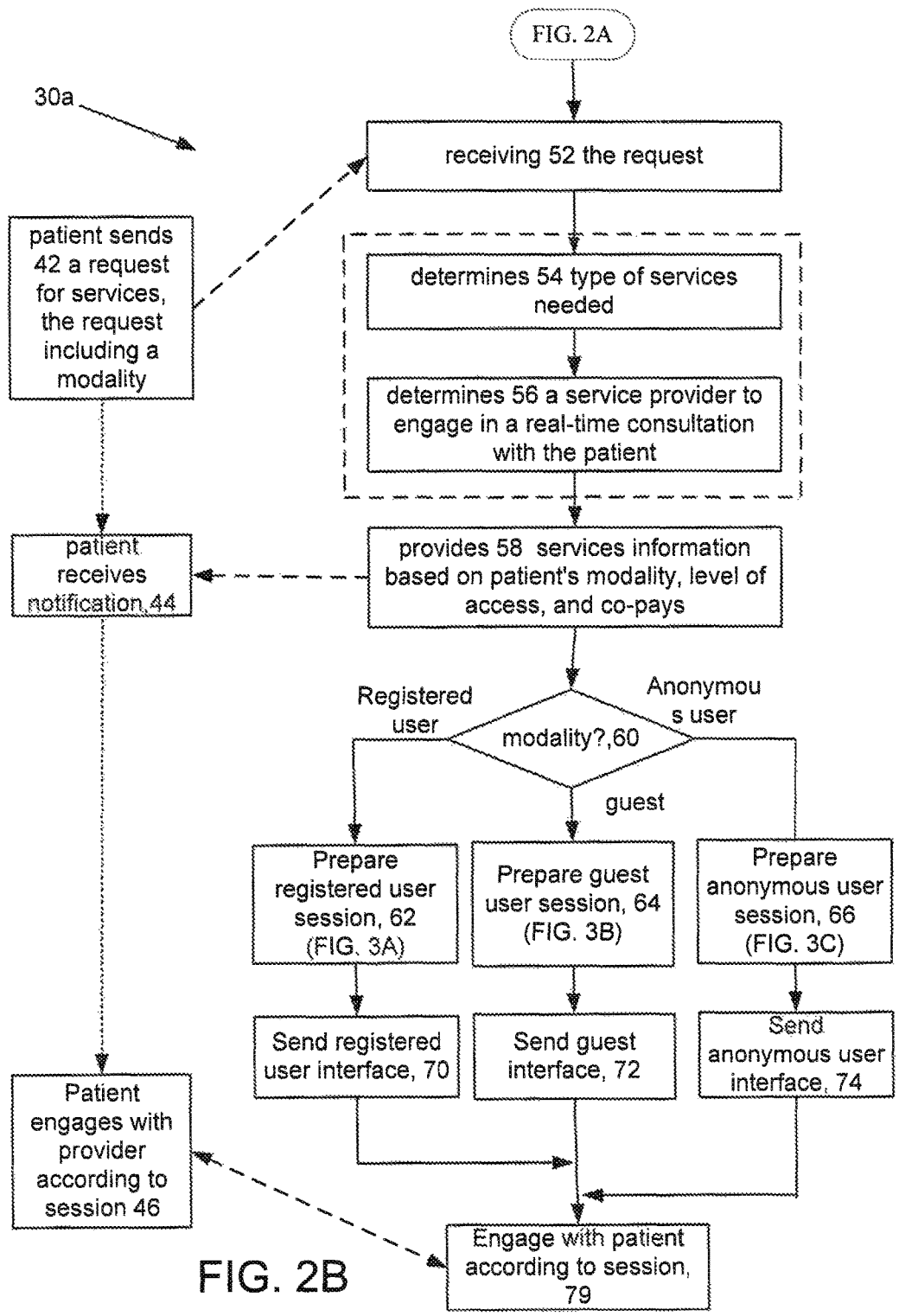

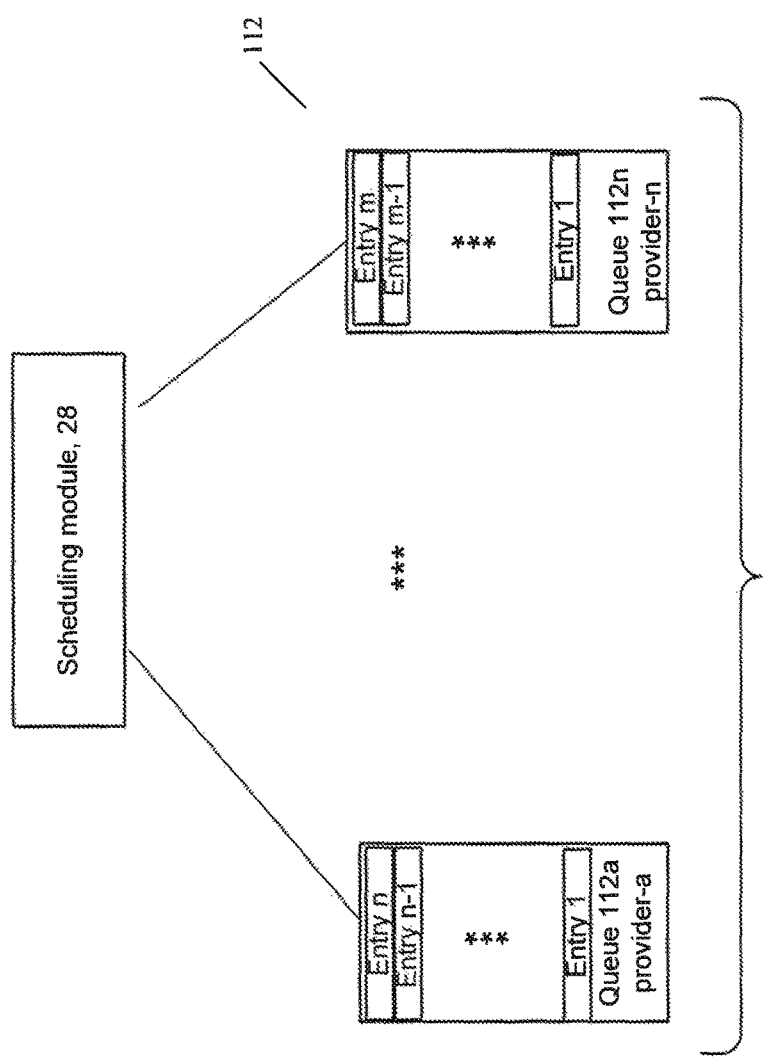
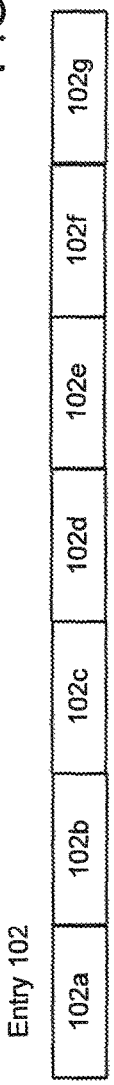

MODALITIES FOR BROKERED ENGAGEMENTS

This application claims priority under 35 U.S.C. §119 to U.S. Provisional Patent Application Ser. No. 61/753,528, filed Jan. 17, 2013, and entitled "Processing for Brokered Engagements", the entire contents of which are hereby incorporated by reference.

BACKGROUND

The present disclosure is directed to connecting consumers with service providers.

Systems have been developed to connect consumers and their providers over the Internet and the World Wide Web. Some systems use e-mail messaging and web-based forms to increase the level of connectivity between a member of a health plan and his assigned health care provider. The consumer sends an e-mail or goes to a website that generates and sends a message (typically an e-mail or an e-mail type message) to a local provider. These types of services have been broadly referred to as "e-visits." Other health care solutions include technologically advanced telephone communication solutions that use advances in voice communication and data transmission technology to interconnect medical professionals with patients.

SUMMARY

According to an aspect, a computer-implemented method includes receiving from a consumer that desires to consult with a service provider, a modality type with the modality type including an anonymous user modality type, with the modality type determining a type of request interface to send to the consumer, receiving from the consumer a request to consult with a service provider, the request including medical information for use during a consultation and with the request based on the modality type selected by the consumer, determining by one or more computers a suitable service provider based on provider availability, that is currently available to engage in a real-time consultation with the consumer, adding by the one or more computers an entry corresponding to the consumer to a queue maintained for the suitable service provider; and when the consumer in the queue is at the top of the queue, causing by the one or more computers establishment of a real-time communication channel with a device used by the consumer.

According to an aspect, a computer program product tangibly stored on a computer readable storage device for providing broker services to consumers and service providers, the computer program product comprising instructions for causing a computer to receive from a consumer that desires to consult with a service provider, an indication of a selected modality type with the modality type including an anonymous user modality type, receive from the consumer a request to consult with a service provider, the request including medical information for use during a consultation and with the request based on the modality type selected by the consumer, determine a suitable service provider based on provider availability, that is currently available to engage in a real-time consultation with the consumer, add an entry corresponding to the consumer to a queue maintained for the suitable service provider; and when the consumer in the queue is at the top of the queue, cause establishment of a real-time communication channel with a device used by the consumer.

According to an additional aspect, an apparatus includes a processor, memory in communication with the processor, and a computer program product stored on a computer readable medium for providing broker services to consumers and service providers, the computer program product comprising instructions for causing the processor to receive from a consumer that desires to consult with a service provider, an indication of a selected modality type with the modality type including an anonymous user modality type, receive from the consumer a request to consult with a service provider, the request including medical information for use during a consultation and with the request based on the modality type selected by the consumer, determine a suitable service provider based on provider availability, that is currently available to engage in a real-time consultation with the consumer, add an entry corresponding to the consumer to a queue maintained for the suitable service provider; and when the consumer in the queue is at the top of the queue, cause establishment of a real-time communication channel with a device used by the consumer.

The following are some of the features within the scope of the above aspects.

The modality types further include a guest user modality type and an enrolled user modality type. An account is established for the user, with the account based on the modality type selected. Anonymous user account type is set up by the system and that contains no personal identifying information for the anonymous user. A guest user type account and an enrolled user type account have personally identifying information of the guest user and enrolled user. The consumer is sent a graphical user interface according to the modality type selected. The graphical user interface for the anonymous user type includes a section that allows a user to type into the graphical interface answers to questions pertaining to their medical status. The questions in graphical user interface for the anonymous user type include a question on a topic that the user wants to discuss, a question on medications that the user is taking and a question on further services that the user needs. The graphical user interface for the anonymous user type specifically excludes payment information. The graphical user interface for the guest user type includes a section that allows a user to type into the graphical interface answers to questions pertaining to their medical status and a section for the guest user to supply payment information.

One or more of the following advantages may be provided by one or more of the above aspects.

Consumers can engage with the system using various modalities, including registered user, guest user and anonymous user. In particular an anonymous user modality is useful for those types of individuals that may have serious issues, but which are generally reluctant to discuss issues with strangers.

BRIEF DESCRIPTION OF THE FIGURES

FIGS. 2A and 2B are flow charts useful in understanding modality processing in a brokerage service.

FIG. 5 shows the relationship of FIGS. 5A and 5B.

FIGS. 5A and 5B are block diagrams of queue structures.

DETAILED DESCRIPTION

Overview

The system described below provides an integrated information and communication platform that enables consumers of services to access service providers to consult and to carry out such consultations in an efficient manner. Consumers are able to consult with an expert service provider even when the two parties are geographically separated. This integrated platform is referred to as a brokerage system (or depending on the context brokerage service).

Figure 1:
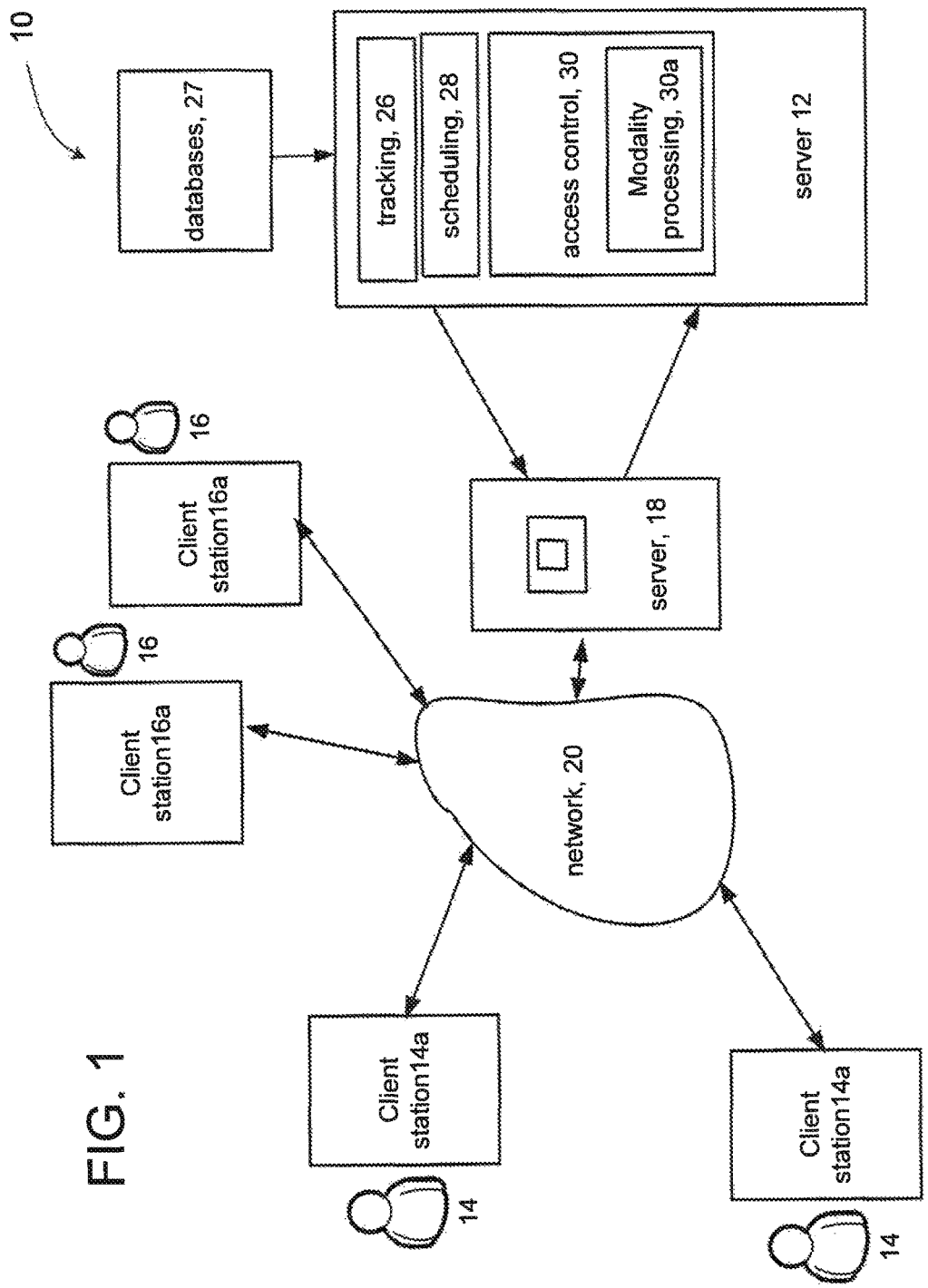
FIG. 1 is a diagrammatic view of a brokerage system.

Referring now to FIG. 1, an exemplary networked computer system 10 including engagement brokerage functionality, includes a computerized system or server 12 for processing requests from consumers 14 at client systems 14a to engage with providers 16 at provider systems 16a. The networked computer system 10 implements a brokerage service embodied as web-based engagement brokerage. The networked computer system 10 includes a web server 18 to receive on-line web-based requests and which provides web-based communication channels between a provider and a consumer using a web browser or the like.

The server 18 receives a request for a consultation a graphical user interface or the like. The request is parsed to identify the particular ailment or concern, etc. of the patient 14. The server 12 includes an availability or presence tracking module 26 for tracking the availability of the service providers 16. Availability or presence is tracked actively or passively. In an active system, one or more of the service providers 16 provides an indication to the server 12 that the one or more service providers are available to be contacted by consumers 14 and an indication of the mode by which the provider may be contacted. In some examples of an active system, the provider's computer, phone, or other terminal device periodically provides an indication of the provider's availability (e.g., available, online, idle, busy) to the server 12 and a mode (e.g., text, voice, video, etc.) by which he can be engaged. In a passive system, the server 12 presumes that the service provider 16 is available by the service provider's actions, including connecting to the server 12 or registering the provider's local phone number with the system. In some examples of a passive system, the server 12 indicates the provider 16 to be available at all times until the provider logs off, except when the provider is actively engaged with a consumer 14.

The server 12 also includes one or more processes in addition to the tracking module 26, such as a scheduling module 28. The server 12 accesses one or more databases 27. The components of the server 12 and the web server 18 may be integrated or distributed in various combinations as is commonly known in the art.

The networked computer system 10 allows a consumer 14 to communicate with a provider 16. The consumer 14 and provider 16 connect to the server 12 through a website or other interface on the web server 18 using client devices 14a and 16a, respectively. Client devices 14a and 16a can be any combination of, e.g., personal digital assistants, cell phones, computer systems, media-player-type devices, and so forth. The client devices 14a and 16a enable the consumers 14 to input and receive information as well as to communicate via video, audio, and/or text with the providers 16.

At the instant a consumer 14 desires to connect and communicate with a provider, the server 12 determines whether that provider is available. If that particular provider 16 is available, the server 12 assesses the various modes of communication that are available forwards connection information of the consumer 14 to the service provider 16 through one or more modes of communication. The system selects a mode of communication to use based in part on the relative utility of the various modes.

A mode of engagement has both the consumer 14 and the provider 16 use web-based consoles, as this allows each of the other modes to be used as needed. For example, consumers and providers may launch chat sessions, voice calls, or video chats from within a web-based console like that shown in FIG. 2A, below. A web based console also provides on-demand access to records, such as the consumer's medical history, and other information. If only one of the participants in an engagement has access to a web console, the server 12 connects that participant's console to whatever form of communication the other party has available. For example, if the consumer is on the phone and the provider is using a web browser, the server 12 may connect the consumer's phone call to a VoIP session that the provider can access through the web. If the provider 16 is not available, the server 12 identifies other available providers 16 that would meet the consumer 14's needs. The server 12 enables the consumer 14 to send a message to the consumer's chosen provider.

The server 12 includes an access control facility 30 that manages and controls whether a particular consumer 14 can access the networked computer system 10 and what level or scope of access to the features, functions, and services the networked computer system 10 will provide. The access control 30 includes modality processing 30a that grants access to consumers according to a modality and thus controls the level of services granted. Different types of patients may engage with the brokerage system using different engagement modalities. For example, the brokerage system 10 enables three different types of modalities, anonymous, guest and registered users. Each type of modality serves needs of different types of patients.

The registered user modality is for users that are either already "enrolled" with the brokerage system 10 or are in the process of enrolling with the brokerage system. Registered users have accounts set up for them on the brokerage system 10. Registered users enter various types of data including personal identifying information (e.g., name, address, etc.) plan information (for billing purposes) and medical information, (a question, ailment, etc.). The brokerage system can retrieve from various sources medical records for registered users, such records being of prior visits by the registered user with the brokerage system or other medical records of the registered user stored at third-party medical record storage sites.

The guest user modality is for users that are not "enrolled" and which do not want to engage with the brokerage system 10 on an ongoing basis, but instead seek to have a single transaction or a series of single transactions. Guest users, as with registered users, can have accounts set up on the brokerage system 10. Guest users enter various types of data including personal identifying information (e.g., name, address, etc.) plan information (for billing purposes) and medical information, (a question, ailment, etc.). The brokerage system can retrieve from various sources medical records for guest users, such records being of prior visits by the guest user with the brokerage system or other medical records of the guest user stored at third-party medical record storage sites.

The "anonymous user modality" is for users that wish to remain anonymous. These users neither want to enroll with the brokerage system 10 nor conduct a series of single transactions. Anonymous users as with registered users can have accounts set up on the brokerage system 10. Anonymous users enter limited data, and specifically exclude personal identifying information (e.g., name, address, etc.) and plan information (for billing purposes). The data is generally limited to medical information (a question, ailment, etc.). As the brokerage system 10, does not know the identities of anonymous users, the brokerage system 10 does not retrieve personal medical records.

However, in some implementations the brokerage can assign anonymous users an account ID. This brokerage system initiated account is set up for internal purposes only. That is, the anonymous user is not assigned either a user name or password. The brokerage system 10 produces records of engagements with anonymous users and references these records to the account ID. The records are maintained for legal purposes only and are not accessed (unless the anonymous user decides at the conclusion of the engagement to actually setup an account and get a username and password.

However, in some implementations the system could send the assigned account ID to the anonymous user to use as a user ID and permit the user to enter a password for follow-on engagements. In those situations, if the anonymous user enters the system assigned account ID, the system retrieves information pertaining to any prior engagement(s) with the anonymous user under that account ID.

Thus, the type of account and content in records of an account would be based on the modality type. Accounts for guest and registered users would include personal identifiable information, whereas at least this type of information would be missing in the anonymous account type.

One advantage that the brokerage provides is that the brokerage system constantly monitors the availability of a provider for an engagement. Thus, consumers regardless of modality receive relatively quick attention to address their questions or concerns. The server 12 can cause a communication channel to be established between the consumer and the provider via a web browser or the like. The server 12 identifies service providers 16 that are available at any given moment to communicate with a consumer about a particular product, service, or related topic or subject, for example, a medical condition.

In order to achieve such a level of availability, the networked computer system 10 assimilates the discretionary or fractional availability windows of time offered by individual providers at stations 16a into a continuous availability perception by consumers. Consumers will have little expectation that the same provider will be constantly available, rather, they expect that some provider will be available.

By way of illustration, the networked computer system 10 services patients that are members of healthcare plans. For example, the service providers 16 may be physicians, and the service consumers 14 may be patients. The service providers and service consumers may also be lawyers and clients, contractors and homeowners, or any other combination of a provider of services and a consumer of services.

The system enables the consumer to search for providers that are available at the time the consumer is searching, and enables the consumer to engage a provider on a transactional basis or for a one-time consultation. A consumer can use the system for various purposes, such as a consultation or second opinion. The system also enables a modality for anonymous user where the system does not obtain personal information from the user and does not bill for the service.

Based on the implementation of the brokerage system, the types of services and the service providers that can be accessed by an anonymous user could be limited without payment for services. Thus, depending on the nature of the engagement (e.g. with physicians vs. nurses), anonymous users may be asked to provide a credit card for billing purposes, in which case the brokerage system would capture the credit card holder's name and billing address, which may correspond to the anonymous user, but the brokerage system still would not require the anonymous user to establish an account on the brokerage system, by obtaining a username and password.

An example of other details of a brokerage system is discussed in my U.S. Pat. No. 7,590,550 entitled: "Connecting Consumers with Service Providers", the contents of which are incorporated herein in its entirety.

Figure 2A:
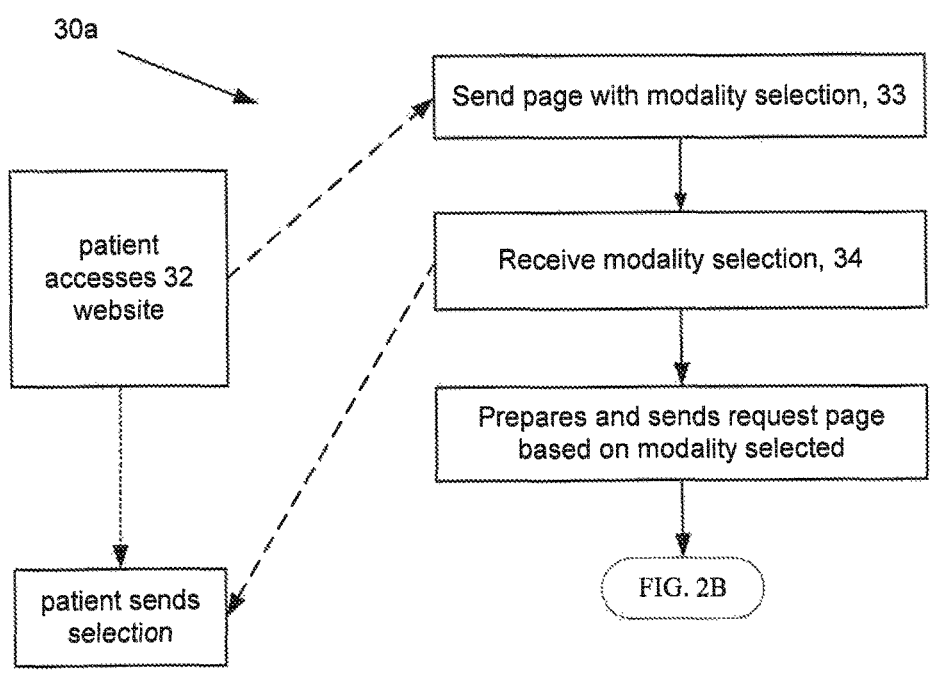

Referring now to FIG. 2A, modality processing 30a for use in the networked computer system 10 is shown. A patient accesses 32 a website of the brokerage system 10. The brokerage system 10 prepares and sends 33 an interface that asks the user how the user desires to engage with the brokerage, e.g., as a registered user, a guest user or an anonymous user. The server receives 34 from the user the selection of modality, and prepares an appropriate request page based on the modality selected.

Referring now to FIG. 2B, in an embodiment, a patient sends 42 the request for services, the request page being prepared or selected based on the modality indicator received from the patient. In some embodiments, an initial request page (not shown) can include the modality indicator. The request is sent to the networked computer system 10 and received by the server 12 for access to an online-care program offered by the system. The server receives 52 the request for services and determines 54 the type of services needed. The server determines 56 a service provider to engage in a real-time consultation with the patient. In some embodiments the server finds a suitable provider based on attribute matching whereas in others the suitable service provider is a provider that is of the type of provider needed for the type of services but is generally the provider with the lowest number of patients waiting. The server places an entry for the patient in a queue discussed below.

The system provides 58 services information to the patient based on patient's modality and determines a session 60 according to modality. When the modality is a registered user, the server 12 prepares a registered user session 62 and sends 70 a registered user interface to the patient. When the modality is a guest user, the server 12 prepares a guest user session 64 and sends 72 a guest user interface to the patient. When the modality is an anonymous user, the server 12 prepares an anonymous user session 66 and sends 74 an anonymous user interface to the patient. The system engages 79 with user according to session type.

Figure 3A:
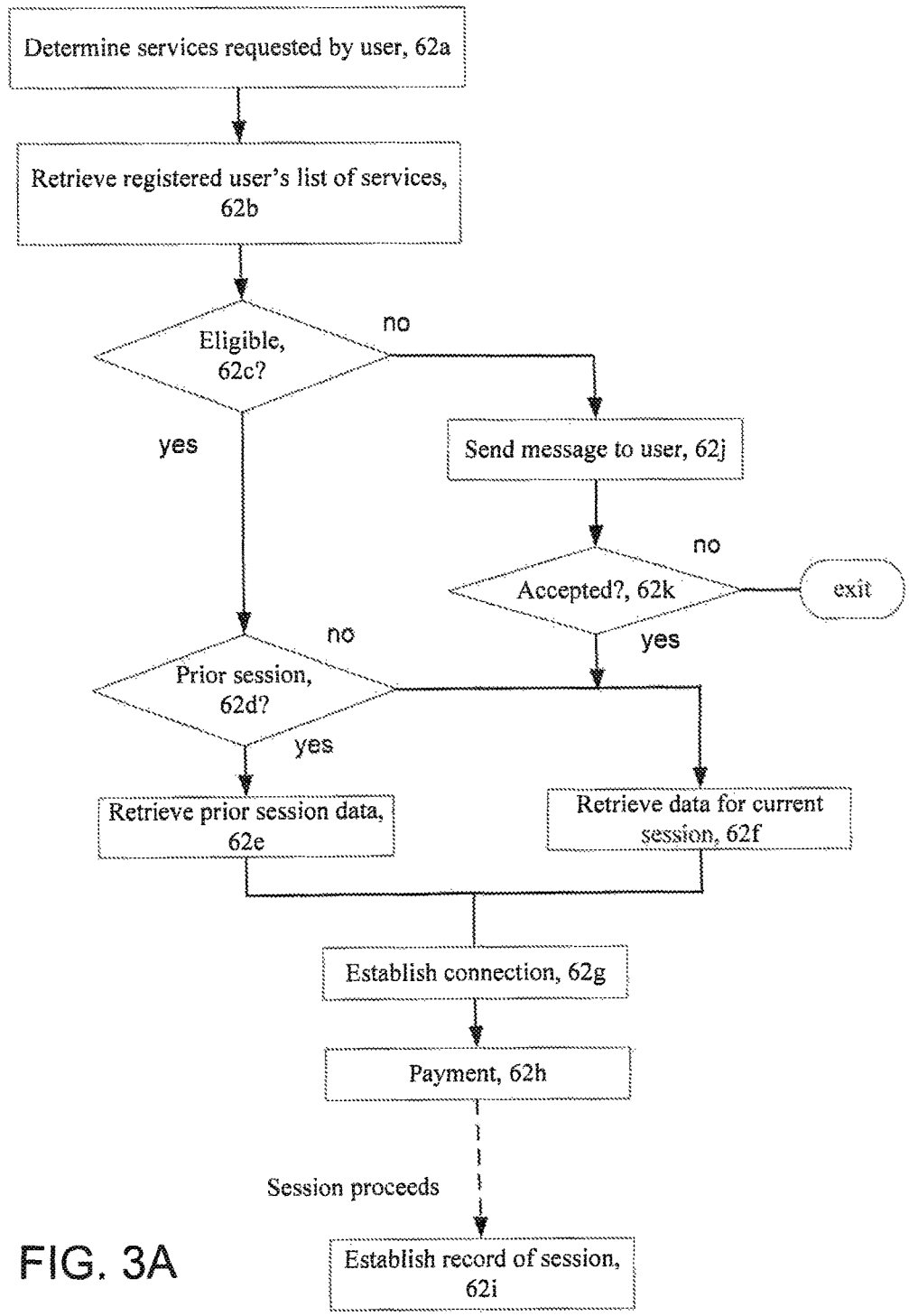
FIGS. 3A-3C are flow chart of session preparation for different modalities.

Referring now to FIG. 3A, the server 12 prepares 62 a registered user session by determining 62a from information received from the patient what services will be required during the session. In one example, for a registered user that is registered through a sponsor, the server 12 retrieves 62b those services that the sponsor has chosen to be offered services. A sponsor selects offered services based on various factors including costs and usage data. Usage data is indicative of an amount of health services being consumed, by consumers, for a particular type of health service. The various factors can also gender, age, health status of the insured, as well as the availability of the services, cost of the services and how often the services were selected by segments of insured groups of individuals.

The system determines 62c whether the registered user is eligible for the determined services by comparing the list of services to the determined services. If eligible, the system determines 62d if the current session is related to a prior session. If the current session is related the system retrieves 62e prior session data. If the current session is not related the system retrieves 62f data for the current session based on the determined services requested. The server establishes 62g (or causes establishment of) a connection. As shown in FIG. 3A, payment can be received 62h by the system after the connection is established. The session with the provider proceeds (indicated by the dashed line) and at the end of the session (not shown) the system establishes 62i a record of the session.

If the registered user is not eligible for the services determined by the system, the system determines if there is any other way to provide the service(s) and/or determines a cost to the registered user for acceptance by the user (not shown). The registered user is sent 62j a message with this information and if accepted 62k goes to retrieved data 62f. Otherwise the system will exit and no session is established.

Figure 3B:
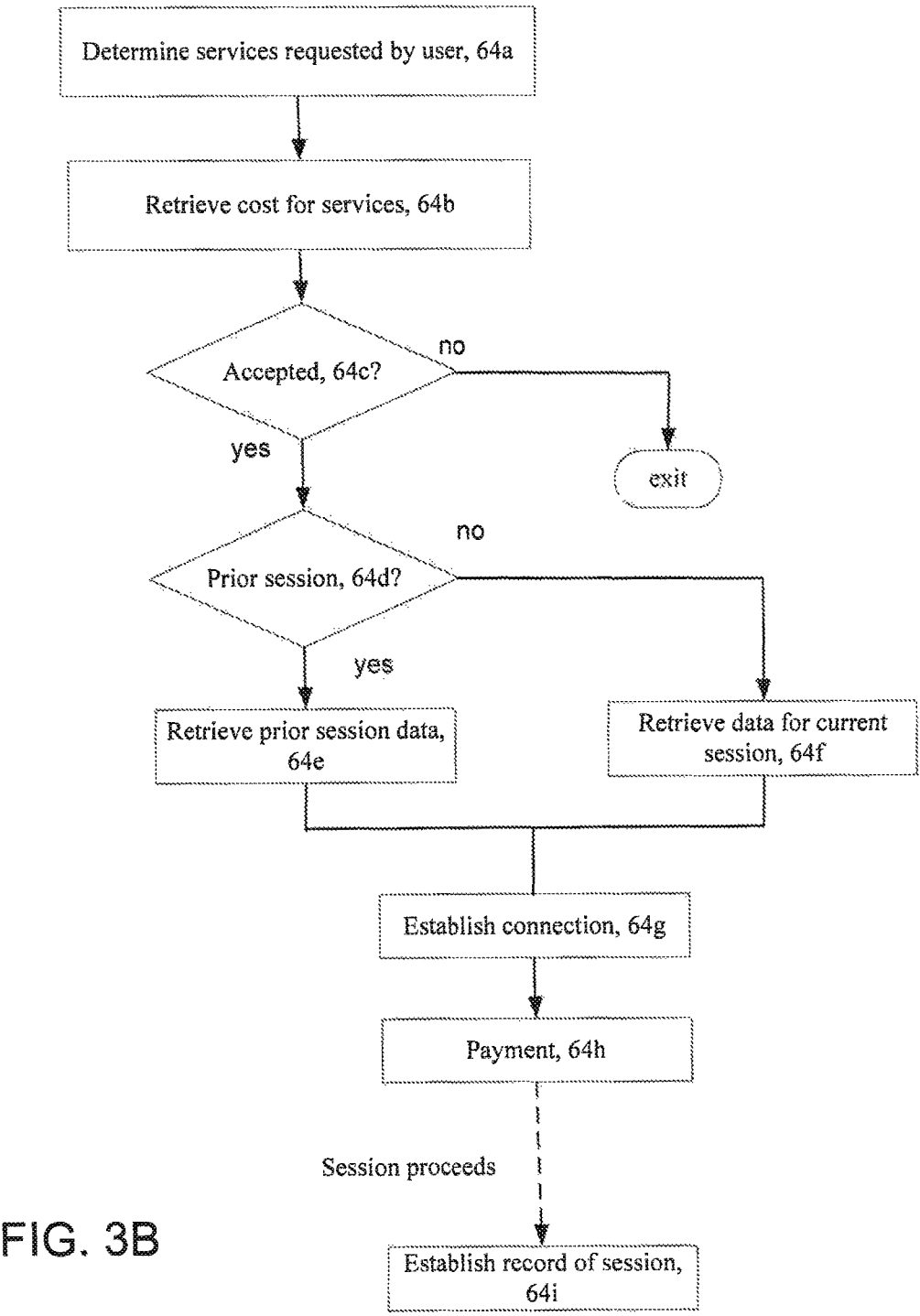

Referring now to FIG. 3B, the server 12 prepares a guest user session 64 by determining 64a from information received from the patient what services will be required during the session. In one example, for a guest user the server 12 determines 64b a cost for those services. If accepted 64c, the system determines 64d whether the current session is related to a prior session. If the current session is related the system retrieves 64e prior session data and can merge with data currently entered by patient. If the current session is not related to any prior session, the system retrieves 64f data for the current session based on the determined services requested. The server establishes 64g (or causes establishment of) a connection. As shown in FIG. 3B, payment can be received 64h by the system after the connection is established. The session with the provider proceeds (indicated by the dashed line) and at the end of the session (not shown) the system establishes 64i a record of the session. If the cost was not accepted 64c, the system exits.

Figure 3C:
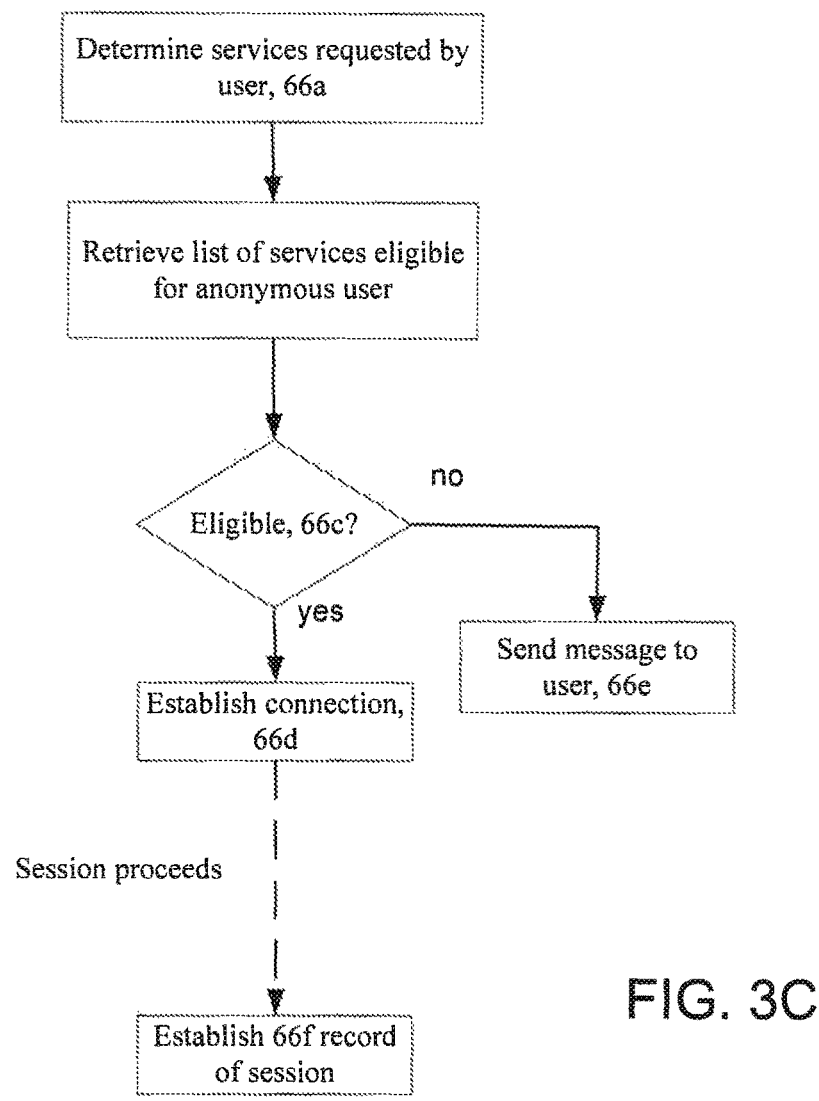

Referring now to FIG. 3C, the server 12 prepares an anonymous user session 66 by determining 66a from information received from the patient what services will be required during the session. In one example, for an anonymous user, the system determines/retrieves 66b a list of services available for an anonymous user and compares 66c to services required, and if eligible, the server 12 establishes 66d (or causes establishment of) a connection. If the service is not eligible, the system sends 66e a message to the anonymous user.

As shown in FIG. 3C, in this implementation there is no payment made to the system 10 by the user. The session with the provider proceeds (indicated by the dashed line) and at the end of the session (not shown) the system establishes 66f a record of the session. With an anonymous user a record of the session includes the system generated identification ID that generally is not shared with the user, but in some implementations the record could be shared in the event there is need for on-going anonymous sessions.

From the provider's viewpoint, the provider chooses a patient from a virtual waiting room. The virtual waiting room can include not only registered user patients, but other patients such as patients that are guest or anonymous users. The system facilitates sessions between the patient and the provider by establishing the real time communication channel between devices/systems used by the patient and the provider with the channel being established through the server 12. In other implementations, the server 12 causes establishment of the communication channel between devices/systems by a join of communication channels or by sending the provider connection information to call the patient in a call back mode.

Figure 4:
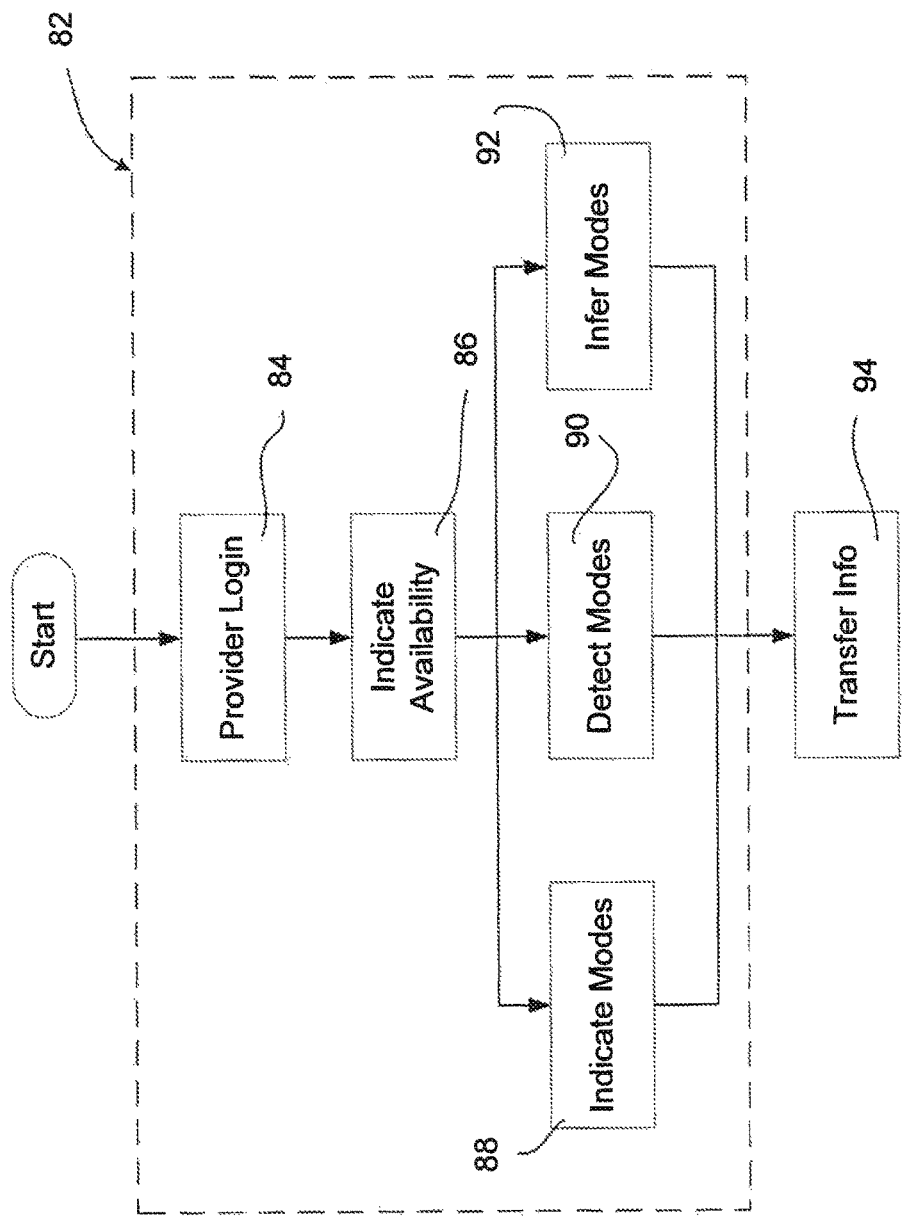
FIG. 4 is block diagram of availability processing.

Referring now to FIG. 4, the server 12 tracks 82 the availability of service providers 16 and in some embodiments, on-line consumers 14. When a provider 16 logs 84 into the networked computer system 10, the provider 16 indicates 86 (such as by setting a check box or selecting a menu entry or by responding to a voice prompt) to the tracking module 26 that he or she is available to interact with consumers 14. The provider 16 can also indicate 88 to the tracking module 26 (such as by setting a check box or selecting a menu entry or by responding to a voice prompt) the modes (e.g., telephone, chat, video conference) by which a consumer 14 can be connected to the provider 16.

The tracking module 26 determines 150 the capabilities of the terminals 14a and 16a the consumer 14 and the provider 16 use to connect to the system (for example, by using a terminal-based program to analyze the hardware configuration of each terminal). Thus, if a provider 16 connects to the networked computer system 10 by a desktop computer and the provider has a video camera connected to that computer, the tracking module 26 determines 90 that the provider 16 can be engaged by text (e.g., chat or instant messenger), voice (e.g., VoIP) or video conference. Similarly, if a provider 16 connects to the system using a handheld device such as a PDA, the tracking module 26 determines 92 that the provider 16 can be engaged by text or voice, whereas, if the consumer connects to the networked computer system 10 via a telephone for a telephonic engagement the provider will reply with a telephone call to the consumer. The tracking module 26 can also infer 92 a provider's availability and modes of engagement by the provider's previously provided profile information and the terminal device through which the provider connects to the system.

Providers participating in the brokerage network can have several states of availability over time. States in which the provider may be available include "on-line", in which the provider is logged-in and can immediately accept new engagements in any mode, "on-line (busy)", in which the provider is logged-in but is currently occupied in another engagement, and "scheduled", in which the provider is offline but is scheduled to be online at a designated timepoint and can pre-schedule engagements for it.

While not online, the provider can take messages as in offline state. Thus, another state includes off-line, in which the provider is not logged in but can take message-based engagements (i.e., asynchronous engagements), out-of-office, in which the provider is not accepting engagements or messages, and "on call", in which the provider is offline and can be paged to go to on-line status by the brokerage network if traffic load demands it (in some examples, consumers see this state as offline).

The operating business model for the provider network employs a remuneration scheme for providers that helps assure that the consumers can find providers in designated professional domains in the online mode. For example, selected providers can be remunerated for being in the on-call mode to encourage on-line availability in case of low discretionary availability by other providers in their professional domain. On-call providers are also called into the on-line state when the fraction of on-line (busy) provider domains exceeds a certain threshold.

Referring now to FIG. 5, queues discussed below are filled by the server 12 with entries 102. These entries can have various fields 102a-102g that represent pointers to or information pertinent to the patient/consumer. More specifically, as consumers access the networked computer system 10 and are processed through the intake process, entries 102 representing the consumers are produced by the server 12 and those entries are queued.

Referring now to FIG. 5A, the tracking module 26 (FIG. 1) transfers 94 (FIG. 4) information about the availability and the communication capabilities of the consumers 14 and the providers 16 to the scheduling module 28. The scheduling module 28 uses the tracking information to schedule providers with consumers. In one scheduling algorithm, each provider is associated with a queue, e.g., 112a-112n. The queue for each provider is filled by the server 12 with entries (as depicted as entry 1, entry n-1 and entry n) for provider 112a and entries (as depicted as entry 1, entry m-1 and entry m) for provider n that represent consumers irrespective of modality that desire to have consultations with the corresponding provider. More specifically, as consumers access the networked computer system 10 and are processed through the intake process, entries representing the consumers are produced by the server 12 and those entries are queued.

In one embodiment, the server 12 stores the entries in queues of those providers that the server 12 determines has the least number of entries, in order to balance provider utilization across the system 10, and to otherwise minimize overall response time for consumers. The server 12 will use a first in first out priority scheme to retrieve records from the query in order to furnish information to providers for servicing clients such as through call-backs.

Thus, in a telephonic engagement the server 12 produces an entry for storage in one of the queues (generally 112). The server 12 examines the queues 112a-112n of all providers that are suitable to provide a consultation with the consumer and the server chooses the queue of a suitable provider that has the least number of entries waiting to be processed. The queue, e.g., queue 112a of the chosen provider (provider-a) is loaded with that entry.

A telephonic call-back engagement can be either one that is a scheduled engagement where the server 12 provides a time for the call-back based on when each of the consumer and provider are available or a non-scheduled call-back based on the available provider.

In servicing consumer requests, for a particular provider, the server 12 retrieves the entry of a consumer that is next to be serviced (generally the oldest entry in the queue 112). As the provider services that consumer, the server 12 removes the corresponding entry from that provider's queue and then the server 12 promotes all remaining entries in that queue such that the next entry in the queue to be serviced will be now be the oldest entry.

Figure 5B:
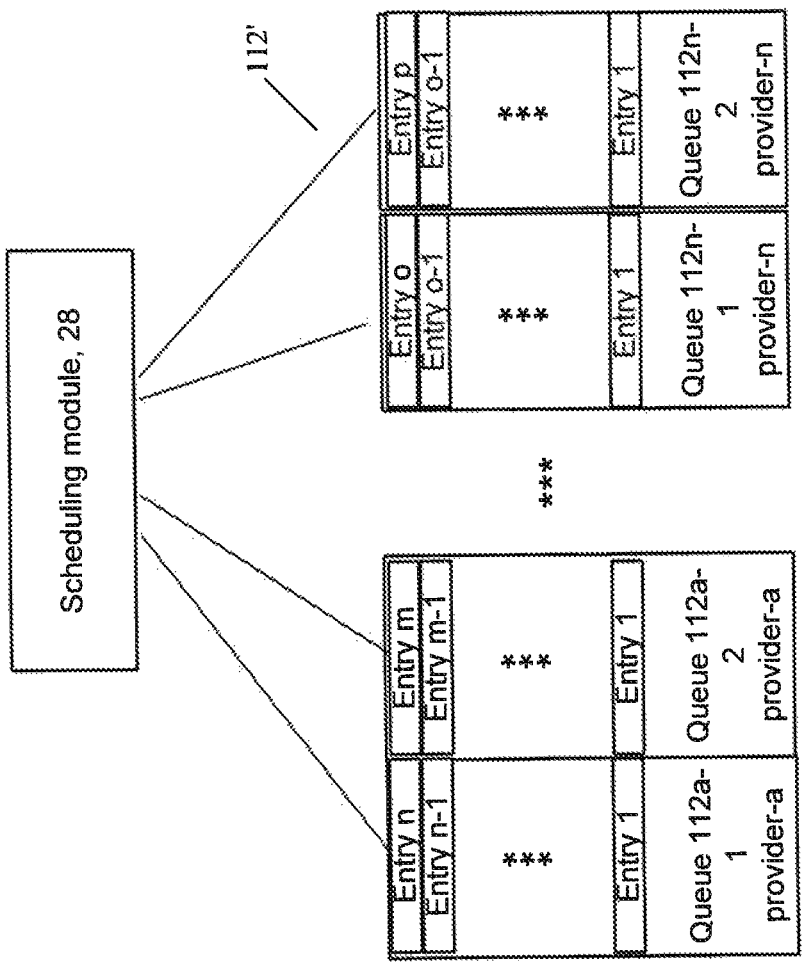

Referring now to FIG. 5B, in an alternative embodiment, the queues (generally 112') for each provider are sub-divided or represented as plural sub-queues with each of the sub-queues corresponding to an appointment "state." In FIG. 5B, two queues 112a-1 to 112a-2 and 112n-1 to 112n-2 are shown for each of the providers, e.g., "provider a" to "provider n" with the sub-queues 112a-1 to 112a-2 and 112n-1 to 112n-2 representing, "waiting room" and "scheduled appointments" of the respective providers "provider a" to "provider n."

In this embodiment, the server using scheduling module 116, examines the queues of all providers that are suitable to provide a consultation with the consumer and chooses the appropriate sub-queue of a suitable provider that has the least number of entries waiting to be processed for the particular state, e.g., "waiting room" and "scheduled appointments." More specifically, for "telephonic engagements" the server loads entries into the waiting room queue of the particular provider that has the fewest entries.

In servicing requests, for a particular provider, the system retrieves the entry of a consumer that is next to be serviced from the waiting room for that provider. The next to be serviced is according to the following priority the oldest entry in the waiting room, unless the server determines that the scheduled appointment queue of the provider has either an entry for a scheduled telephonic callback or scheduled appointment that has an scheduled appointment time that is either equal to the current time or would be within a time window where the servicing of a waiting room entry or a new request would adversely impact servicing of scheduled telephonic callback or scheduled appointment queued entries. For example, in some embodiments the system 10 could allocate a set time period of, e.g., 15 minutes to service a request. Accordingly, the server 12 would not select an entry from the waiting room queue if there was a scheduled appointment in, e.g., 10 minutes. Telephonic engagements without any scheduling will generally be placed in and thus serviced from the waiting room sub-queue.

As the provider services a consumer from its sub-queue all remaining entries (representing other consumers) in that sub-queue are promoted such that the next entry in the sub-queue to be serviced will be the next oldest entry.

In another embodiment, the server 12 stores all incoming telephonic call-back engagements in a waiting room queue along with other types of engagements. One queue is used for all providers and the scheduling module 28 examines the queue and chooses the provider that is next available.

Figure 6:
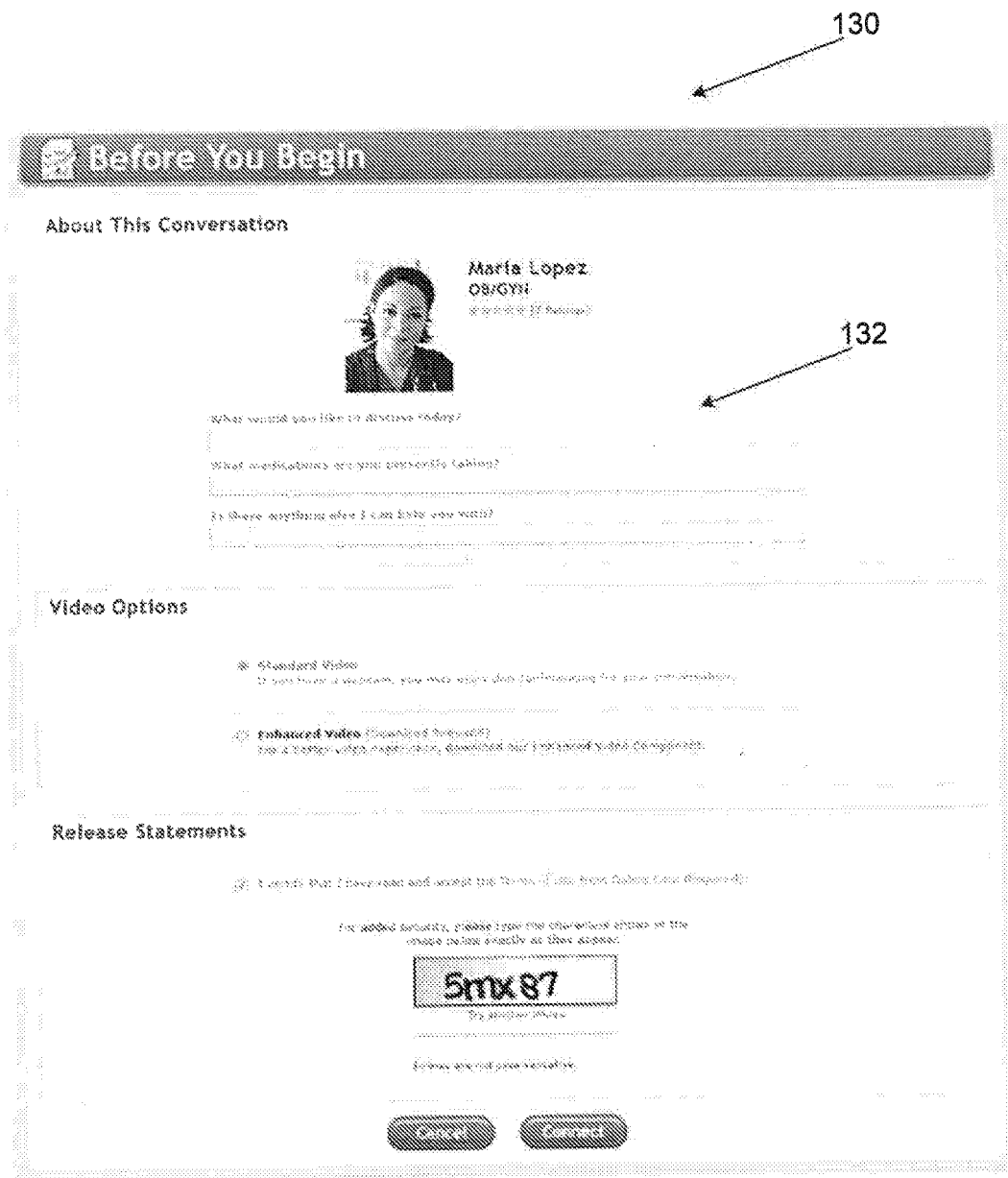
FIG. 6 is a screenshot of a graphical user interface for anonymous users.
Figure 7A:
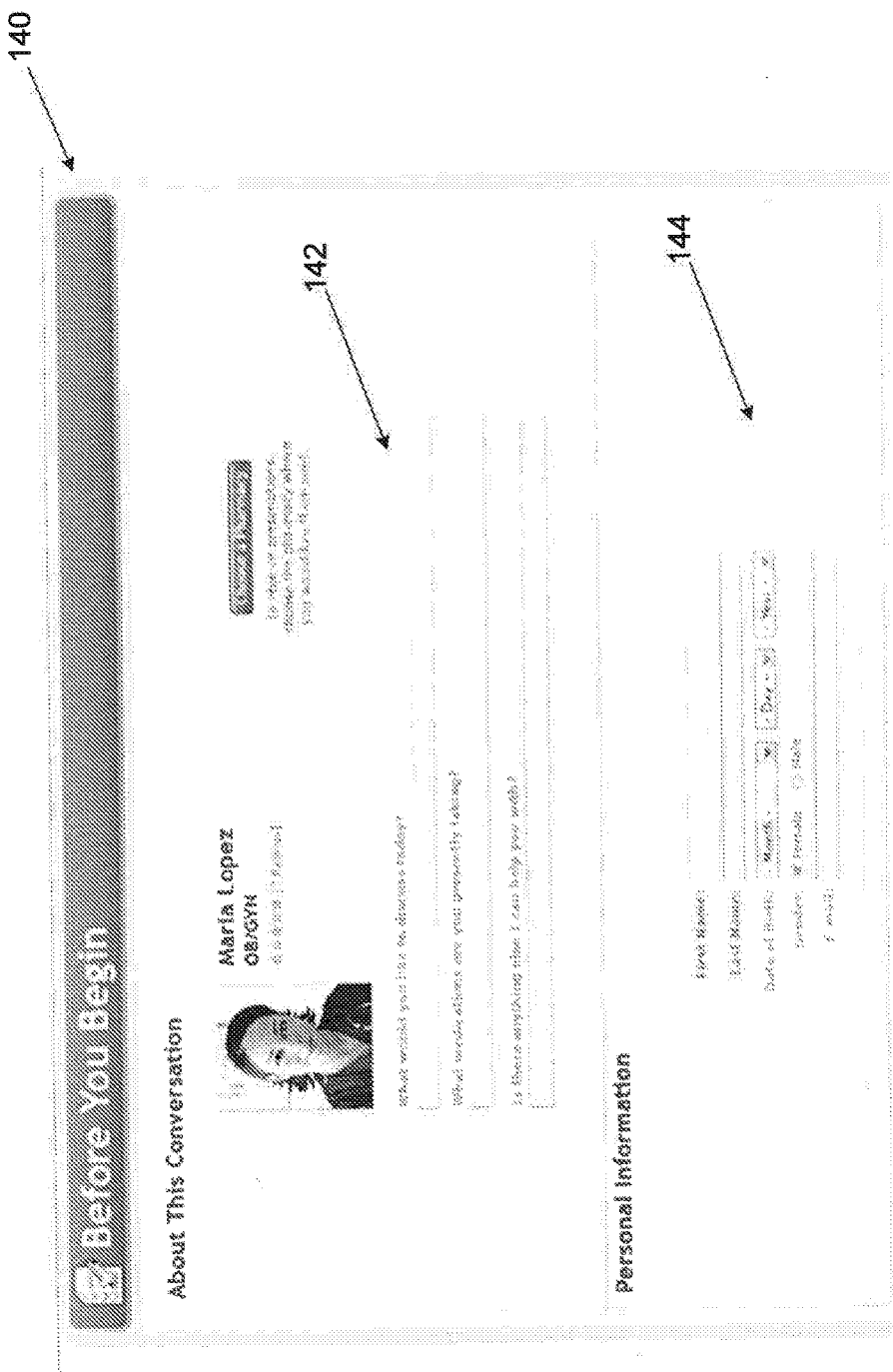
FIGS. 7A to 7C are screenshots of a graphical user interface for guest users.
Figure 7B:
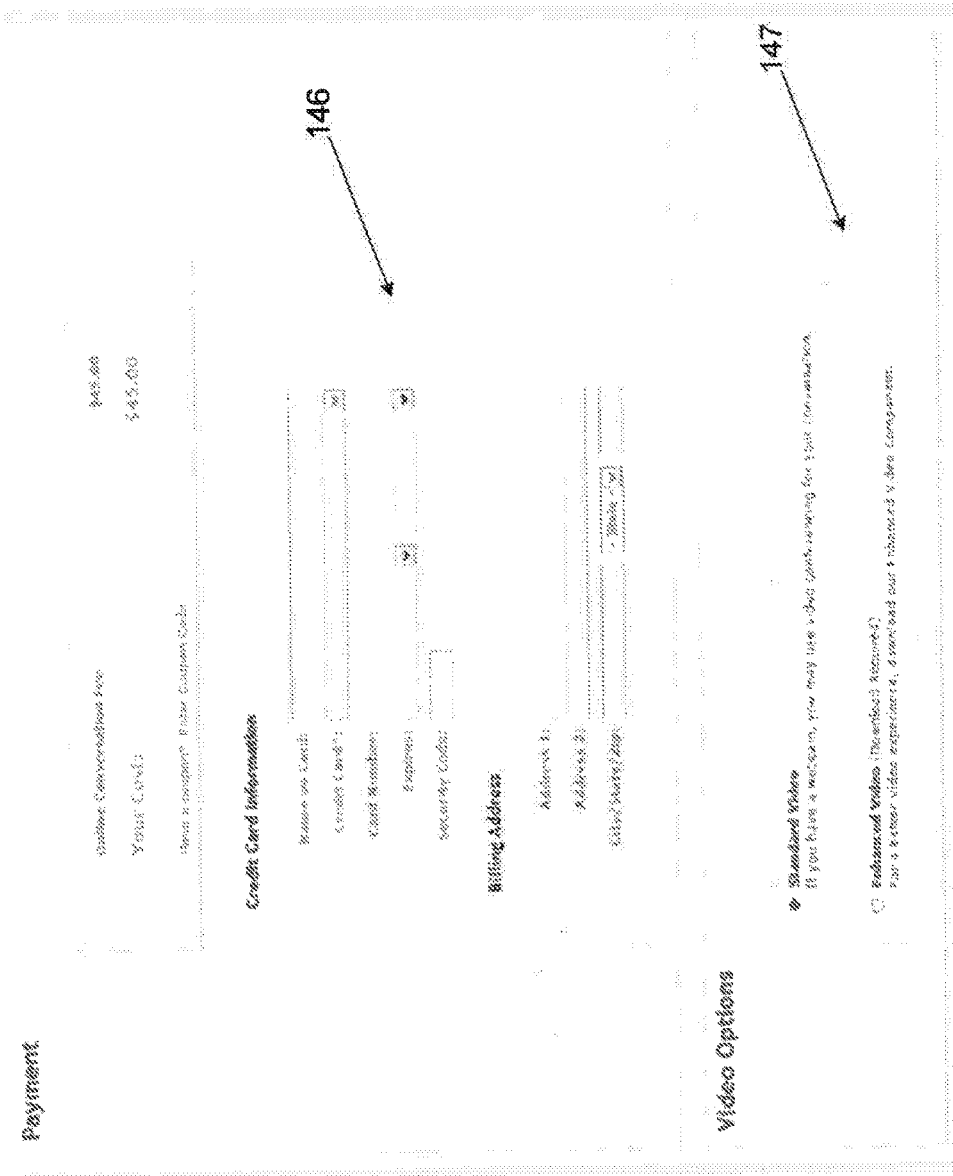
Figure 7C:
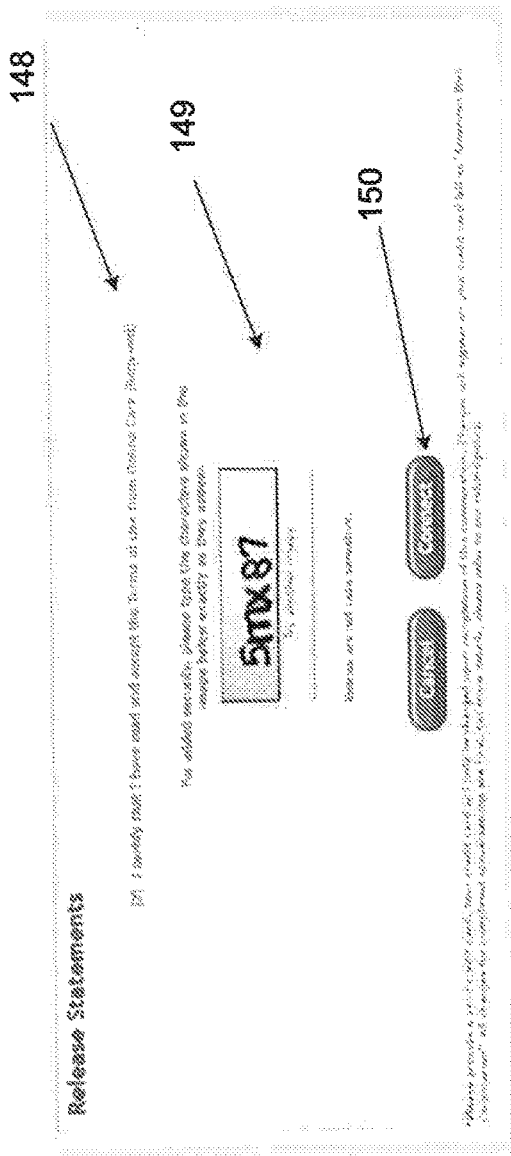
Figure 7:
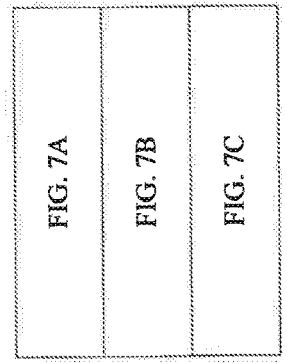
FIG. 7 shows the relationship with FIGS. 7A-7C.

Referring now to FIG. 6, a graphical user interface 130 for an anonymous user has the consumer enter information regarding the consumer's ailment or question in fields 132. Exemplary information would be a question regarding what the consumer would like to discuss, a question on medications and if there is anything else that the consumer would like to discuss. The interface 130 also presents the user with video options and likewise presents a release statement and a challenge. The connect button can be used to initiate the real-time communication channel with the selected provider (shown in the interface).

Referring now to FIGS. 7 and 7A-7C, a graphical user interface 140 for a guest user has fields 142 for the consumer to enter information regarding the consumer's ailment or question. Exemplary information would be a question regarding what the consumer would like to discuss, a question on medications and if there is anything else that the consumer would like to discuss, similar as depicted above for the anonymous user interface 130. The graphical user interface 140 also has a region 144 for personal information and payment information 146 (unlike the anonymous user interface 130). The interface 140 also presents the user with video options 147 and likewise presents a release statement 148 and a challenge 149 and a connect button 150. The connect button 150 can be used to initiate the real-time communication channel with the selected provider.

As noted, the server 12 includes access control facilities 114 that control how consumers 14 access the system and to what extent or level the services provided by the system are made available to consumers. The server 12 also stores and provides access to consumer information (e.g., contact information, credit and financial information, credit card information, health information, and other information related to the consumer and the services purchased or otherwise used by the consumer) and provider information (e.g., physician biographies, product and service information, health related content and information and any information the provider or the health plan wants to make available to members) and the access control facility 114 can prevent unauthorized access to this information. In some examples, the server 12 exports the consumer information for use in a provider's office or other facility.

In some embodiments, consumers may select providers according to attributes of the provider, such as a geographical area where the provider is located or which professional organizations have accredited the provider (e.g., whether a doctor has board certification in cardiology). Any metrics within the provider profile can be used to define a list of providers that meet the consumer's preferences. In this case, the system will use the consumer's selection to override the least used scheme for populating provider queues.

Modes of Engagement

Telephonic callbacks—Consumers who wish for a telephonic consultation with a provider may use a traditional telephone to enter information, as discussed above, and hangs up and waits for a call-back from a suitable provider, as also discussed above. Providers are sent information concerning the consumer in order to understand the consumer's issue and a telephone number by which the provider contacts the consumer.

In some embodiments of the networked computer system 10, the networked computer system 10 allows consumers to engage provider's e.g., health professionals "on demand" based on provider availability. These engagements can be established in various ways as described in the above mentioned patent. These types of engagements include:

Passive browsing—Reference health content is accessed on the brokerage's website. The website can support the use of licensed content packages from other vendors to meet the variable preferences of health plans. For example, key content vendors include Healthwise™, ADAM™, Mayo Clinic™ and HealthDay™. Content libraries provided by such vendors offer a combination of articles, imagery, interactive tutorials and related tools that allow consumers to access content relevant for their health issues. Many health plans and major employers already possess a license for the use of one of these content packages.

Health Risk Assessments—The system acquires information from consumers through automated interaction (e.g., rules-based interaction) in order to crystallize their needs (e.g., medical risks) and better direct them. Assessments span from general health to very specific medical conditions and follow a path of questioning that dynamically tailors itself based on information already retrieved (e.g., using predefined rules). As assessments progress, the system constructs engagement suggestions that the consumer can exercise. Each suggestion represents both the question to the provider and the type of provider appropriate to answer it. Consumers may choose to simply launch such engagements or apply their own discretion as to the phrasing and the selection of the recipient provider. This is discussed in more detail below in the context of the consumer advisor.

Asynchronous correspondence—The lowest level of true provider interaction is by way of secure messaging. The question or topic of the engagement is sent to a selected provider (whether online or not) and can be answered by this provider at her leisure. Turnaround times are monitored by the system and are part of the credentials of the provider used for her selection by consumers. The system informs the consumer once a response has been received and can allow the consumer to redirect the question if he needs more urgent response time. For example, typical types of asynchronous correspondence include e-mail, instant messaging, text-messaging, voice mail messaging, VoIP messaging (i.e., leaving a message using VoIP), and paper letters (e.g., via the U.S. Postal Service).

Synchronous correspondence—Several forms of synchronous correspondence allow the consumer and the provider to engage in real-time discussions.

Synchronous text correspondence—This may be referred to as a "Chat" module where both sides of the engagement type their entries in response to each others' entries. The form of communication may be entirely text based but is still a live communication. Examples include instant messaging and SMS messaging.

Web-based teleconferencing—The use of broadband network connections allows for real-time voice transmission over the Internet in what is referred to as full duplex (i.e., both voice channels are open at the same time). Consumers can opt to have a voice conversation with their providers using, for example, their computer's speakers and microphone. Web-based teleconferencing may use VoIP, SIP, and other standard or proprietary technologies.

Telephonic conferencing—Consumers who wish for a direct telephonic communication with a provider or who are not comfortable using their computer may use a traditional telephone for interaction with a provider. The consumer may use a dial-in number and an access code that connects him to the brokerage's servers. Providers are linked to the servers via VoIP, other data-network-based voice systems, or their own telephones. Telephonic conferencing may also allow consumers to request "call me now" functions, in which the provider calls the consumer (directly or through the brokerage).

Video conferencing—The system can support video conferencing to allow consumers to exhibit physical findings to providers if such disclosure is needed. Consumers and providers may also simply prefer face-to-face communication, even if remote. Small digital cameras, referred to as webcams, attached to or built in to personal computers or laptops can be used for this purpose. Video conferencing can be provided by standard software or by custom software provided by the brokerage. Alternatively, dedicated video conferencing communication equipment or telephones with built-in video capabilities can be used.

Semi synchronous correspondence—Some engagements of a consumer with an online provider include both synchronous and asynchronous interactions. Part of the engagement takes place by immediate messaging between the two, but the provider may ask the consumer to take occasional asynchronous assessments if, for example, a generic line of question is desired. This allows the provider to operate more than one consumer engagement at a time while each consumer is constantly engaged. For example, semi-synchronous correspondence includes a combination of e-mail, instant messaging, test messaging, voice calls and mail messaging, and VoIP calls and VoIP messaging.

Interactive Voice Response Engagements

Interactive Voice Response (IVR) systems allow for the deployment of interactive audio menus over the phone. The caller can navigate between options, listen to data-driven information, provide meaningful input, and engage system functions. IVR engagements extend the reach of the system to the telephone as a portable consumer interface to launch an engagement in addition to the Web-based interface. Consumers select a pin code on the application to authenticate their identity if they call in. Several types of engagements can be carried out through an IVR system using suitable logic such as described in the Patent. For dial-in engagements, the consumer calls in and invokes a telephonic engagement with an available provider. The IVR system extends the consumer's ability to select a provider to the phone so that the consumer's interaction resembles one carried out on the Web.

The IVR system can also be used proactively to pursue consumers who need a follow-up. At the time of a follow-up, the system recalls the provider with whom the follow-up is desired (or the type of provider in case the follow-up is not restricted to a specific provider), identifies that the provider is available for an engagement, and attempts to contact the consumer over the phone to establish a connection for the engagement. Once contacted, the consumer can decline or ask postpone the call. If the consumer takes the call, the connection is made. When consumers are pursuing an engagement with a provider that is either busy or currently offline, the IVR system allows the consumer to park in a standby mode until the provider is available. When the provider is available, the system calls the consumer, identifies the provider to the consumer, and verifies that the consumer is still interested in pursuing the call with the provider. If the consumer is still interested, an engagement is connected.

In addition to launching engagements, the IVR interface allows consumers to interact with other services offered by the brokerage. For example, consumers can instruct the system to fax a transcript of their information to a fax machine that the consumer identifies by keying in or speaking its phone number. Using such a function, a consumer makes key information available to, e.g., emergency room personnel or to a provider in an office visit, without the need to plan, collect, print, and carry the information to that encounter.

IVR hardware is readily available from telecommunication vendors and can be programmed to operate in the context of the brokerage framework. Authentication is provided through a PIN number or by other standard methods.

The consumer information collected by the intake process may be stored in the databases 118 as part of the overall brokerage. In some examples, the consumer information is protected and secured from unauthorized access and in compliance with the various legal requirements for storing private consumer information (for example, HIPPA governs access to an individual's health care information). The database 118 may also the process logic and rules data including the business logic of an application or rules for a rules engine that implements the consumer advisor module.

The brokerage extends the result of any engagement to a physical point of care or service provider to allow continuation or escalation of services beyond those provided in the electronic encounter.

Embodiments can be implemented in digital electronic circuitry, or in computer hardware, firmware, software, or in combinations thereof. Apparatus of the invention can be implemented in a computer program product tangibly embodied or stored in a machine-readable storage device for execution by a programmable processor; and method actions can be performed by a programmable processor executing a program of instructions to perform functions of the invention by operating on input data and generating output. The invention can be implemented advantageously in one or more computer programs that are executable on a programmable system including at least one programmable processor coupled to receive data and instructions from, and to transmit data and instructions to, a data storage system, at least one input device, and at least one output device. Each computer program can be implemented in a high-level procedural or object oriented programming language, or in assembly or machine language if desired; and in any case, the language can be a compiled or interpreted language.

Suitable processors include, by way of example, both general and special purpose microprocessors. Generally, a processor will receive instructions and data from a read-only memory and/or a random access memory. Generally, a computer will include one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD ROM disks. Any of the foregoing can be supplemented by, or incorporated in, ASICs (application-specific integrated circuits).

Other embodiments are within the scope and spirit of the description claims. For example, due to the nature of software, functions described above can be implemented using software, hardware, firmware, hardwiring, or combinations of any of these. Features implementing functions may also be physically located at various positions, including being distributed such that portions of functions are implemented at different physical locations.

What is claimed is:

1. A computer-implemented method for automatically establishing online communication sessions in accordance with logic and rules data specifying types of communication sessions for a plurality of modality types, comprising:

receiving, by an online system, from a consumer that desires to consult with a service provider, information specifying a modality type of the consumer for an online consultation via the online system, with the modality type specifying whether the consumer is an anonymous user of the online system or an enrolled user of the online system, with the modality type determining a type of graphical user interface to send to the consumer, with the online system being a networked system connected to the Internet for electronically matching consumers and providers of services in a networked environment;

obtaining logic and rules data that define:
one or more first levels of service that are authorized for a first modality type of the plurality;
one or more first types of communication sessions that are authorized for the first modality type;
a first type of graphical user interface for the first modality type;
one or more second levels of service that are authorized for a second modality type of the plurality;
one or more second types of communication sessions that are authorized for the second modality type; and
a second type of graphical user interface for the second modality type;

determining, based on the specified modality type, one or more online services for which the consumer is eligible to receive through the online system and a type of communication session that is in accordance with the specified modality type, with the types of services being offered through the online system varying based on modality type, with one or more types of services offered for the anonymous user modality type differing from one or more types of services offered for the enrolled user modality type by evaluating the received information specifying the modality type against the logic and rules data obtained;

preparing, by the online system, an online communication session for the specified modality type, with the online communication session being a first type of online communication session when the consumer is an anonymous user and with the online communication session being a second, different type of online communication session when the consumer is an enrolled user, and with the online communication session being based on the types of services for which the consumer is eligible;

based on the evaluating the received information specifying the modality type against the logic and rules data obtained,
selecting, by the online system from among a plurality of different interfaces for different modality types, a graphical user interface for the modality type of the consumer, with a graphical user interface for the anonymous user modality type differing from a graphical user interface for the enrolled user modality type;

transmitting, to a client device of the consumer, the selected graphical user interface for the modality type of the consumer for rendering on a display of the client device;

receiving from the consumer, based on the transmitted user interface, a request to consult with a service provider, the request including medical information for use during a consultation and with the request based on the modality type selected by the consumer;

detecting one or more network connections to the online system through one or more terminal devices of one or more service providers;

automatically tracking online, real-time, current availability for medical service providers, with the tracking being by a tracking module of the online system based on the one or more detected network connections between the online system and the one or more terminal devices, real-time, current availability for medical service providers, with the current availability specifying whether a service provider is online and otherwise not engaged in a consultation;

based on the tracking, generating contact data for a suitable service provider that is currently available to engage in a real-time online consultation with the consumer; and applying the contact data for the suitable service provider to communication session data representing the type of communication session determined from logic and rules data to establish a real-time communication channel with a device used by the consumer.

2. The method of claim 1, wherein modality types further comprise a guest user modality type.

3. The method of claim 2, further comprising:
establishing an account for the user, with the account based on the modality type selected.

4. The method of claim 3 wherein an anonymous user account type is set up by the system and that contains no personal identifying information for the anonymous user.

5. The method of claim 2, wherein a guest user type account and an enrolled user type account have personally identifying information of the guest user and enrolled user.

6. The method of claim 2 wherein a graphical user interface for a guest user modality type comprises:

a section that allows a user to type into the graphical interface answers to questions pertaining to their medical status; and
a section for the guest user to supply payment information.

7. The method of claim 1 wherein the graphical user interface for the anonymous user type includes a section that allows a user to type into the graphical interface answers to questions pertaining to their medical status.

8. The method of claim 7 wherein the questions in graphical user interface for the anonymous user type include a question on a topic that the user wants to discuss, a question on medications that the user is taking and a question on further services that the user needs.

9. The method of claim 1 wherein the graphical user interface for the anonymous user type specifically excludes payment information.

10. A computer program product tangibly stored on a computer readable storage device for automatically establishing online communication sessions in accordance with logic and rules data specifying types of communication sessions for a plurality of modality types, the computer program product comprising instructions for causing a computer of an online system to:

receive, by the online system, from a consumer that desires to consult with a service provider, information specifying a modality type of the consumer for an online consultation via the online system, with the modality type specifying whether the consumer is an anonymous user of the online system or an enrolled user of the online system, with the modality type determining a type of graphical user interface to send to the consumer, with the online system being a networked system connected to the Internet for electronically matching consumers and providers of services in a networked environment;

obtain logic and rules data that define:
one or more first levels of service that are authorized for a first modality type of the plurality;
one or more first types of communication sessions that are authorized for the first modality type;
a first type of graphical user interface for the first modality type;
one or more second levels of service that are authorized for a second modality type of the plurality;
one or more second types of communication sessions that are authorized for the second modality type; and
a second type of graphical user interface for the second modality type;

determine, based on the specified modality type, one or more online services for which the consumer is eligible to receive through the online system and a type of communication session that is in accordance with the specified modality type, with the types of services being offered through the online system varying based on modality type, with one or more types of services offered for the anonymous user modality type differing from one or more types of services offered for the enrolled user modality type by evaluating the received information specifying the modality type against the logic and rules data obtained;

prepare, by the online system, an online communication session for the specified modality type, with the online communication session being a first type of online communication session when the consumer is an anonymous user and with the online communication session being a second, different type of online communication session when the consumer is an enrolled user, and with the online communication session being based on the types of services for which the consumer is eligible;

based on the evaluating the received information specifying the modality type against the logic and rules data obtained, select, by the online system from among a plurality of different interfaces for different modality types, a graphical user interface for the modality type of the consumer, with a graphical user interface for the anonymous user modality type differing from a graphical user interface for the enrolled user modality type;

transmit, to a client device of the consumer, the selected graphical user interface for the modality type of the consumer for rendering on a display of the client device;

receive from the consumer, based on the transmitted user interface, a request to consult with a service provider, the request including medical information for use during a consultation and with the request based on the modality type selected by the consumer;

detect one or more network connections to the online system through one or more terminal devices of one or more service providers;

automatically track online, real-time, current availability for medical service providers, with the tracking being by a tracking module of the online system based on the one or more detected network connections between the online system and the one or more terminal devices, real-time, current availability for medical service providers, with the current availability specifying whether a service provider is online and otherwise not engaged in a consultation;

based on tracking, generate contact data for a suitable service provider that is currently available to engage in a real-time online consultation with the consumer; and apply the contact data for the suitable service provider to communication session data representing the type of communication session determined from logic and rules data to establish a real-time communication channel with a device used by the consumer.

11. The product of claim 10, wherein modality types further comprise a guest user modality type.

12. The product of claim 11 wherein a guest user type account and an enrolled user type account have personally identifying information of the guest user and enrolled user.

13. The product of claim 10 further comprises instructions to:
establish an account for the user, with the account based on the modality type selected.

14. The product of claim 10 further comprising instructions to set up an anonymous user account type by the processor, with the anonymous user account type containing no personal identifying information for the anonymous user.

15. The product of claim 10 with the graphical user interface for the anonymous user type specifically excluding payment information.

16. An apparatus of an online system for automatically establishing online communication sessions in accordance with logic and rules data specifying types of communication sessions for a plurality of modality types, the apparatus comprising:

a processor;
memory in communication with the processor; and
a computer program product stored on a computer readable medium, the computer program product comprising instructions for causing the processor to:

receive, by the online system, from a consumer that desires to consult with a service provider, information specifying a modality type of the consumer for an online consultation via the online system, with the modality type specifying whether the consumer is an anonymous user of the online system or an enrolled user of the online system, with the modality type determining a type of graphical user interface to send to the consumer, with the online system being a networked system connected to the Internet for electronically matching consumers and providers of services in a networked environment;

obtain logic and rules data that define:
  one or more first levels of service that are authorized for a first modality type of the plurality;
  one or more first types of communication sessions that are authorized for the first modality type;
  a first type of graphical user interface for the first modality type;
  one or more second levels of service that are authorized for a second modality type of the plurality;
  one or more second types of communication sessions that are authorized for the second modality type; and
  a second type of graphical user interface for the second modality type;

determine, based on the specified modality type, one or more online services for which the consumer is eligible to receive through the online system and a type of communication session that is in accordance with the specified modality type, with the types of services being offered through the online system varying based on modality type, with one or more types of services offered for the anonymous user modality type differing from one or more types of services offered for the enrolled user modality type by evaluating the received information specifying the modality type against the logic and rules data obtained;

prepare, by the online system, an online communication session for the specified modality type, with the online communication session being a first type of online communication session when the consumer is an anonymous user and with the online communication session being a second, different type of online communication session when the consumer is an enrolled user, and with the online communication session being based on the types of services for which the consumer is eligible;

based on the evaluating the received information specifying the modality type against the logic and rules data obtained, select, by the online system from among a plurality of different interfaces for different modality types, a graphical user interface for the modality type of the consumer, with a graphical user interface for the anonymous user modality type differing from a graphical user interface for the enrolled user modality type;

transmit, to a client device of the consumer, the selected graphical user interface for the modality type of the consumer for rendering on a display of the client device;

receive from the consumer, based on the transmitted user interface, a request to consult with a service provider, the request including medical information for use during a consultation and with the request based on the modality type selected by the consumer;

detect one or more network connections to the online system through one or more terminal devices of one or more service providers;

automatically track online, real-time, current availability for medical service providers, with the tracking being by a tracking module of the online system based on the one or more detected network connections between the online system and the one or more terminal devices, real-time, current availability for medical service providers, with the current availability specifying whether a service provider is online and otherwise not engaged in a consultation;

based on tracking, generate contact data for that is currently available to engage in a real-time online consultation with the consumer; and apply the contact data for the suitable service provider to communication session data representing the type of communication session determined from logic and rules data to establish a real-time communication channel with a device used by the consumer.

17. The apparatus of claim 16, wherein the computer program product further comprises instructions to:
   establish an account for the user, with the account based on the modality type selected.

18. The apparatus of claim 16, wherein the computer program product further comprises instructions to:
   set up an anonymous user account type by the processor, with the anonymous user account type containing no personal identifying information for the anonymous user.

19. The apparatus of claim 16 with the graphical user interface for the anonymous user type specifically excluding payment information.

* * * * *